(12) United States Patent
Knaack et al.

(10) Patent No.: US 7,985,414 B2
(45) Date of Patent: Jul. 26, 2011

(54) POLYURETHANES FOR OSTEOIMPLANTS

(75) Inventors: David Knaack, Summit, NJ (US); John Winterbottom, Jackson, NJ (US); David Kaes, Toms River, NJ (US); Todd Boyce, Matawan, NJ (US); Larry Shimp, Morganville, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1459 days.

(21) Appl. No.: 11/336,127

(22) Filed: Jan. 19, 2006

(65) Prior Publication Data

US 2006/0216323 A1    Sep. 28, 2006

Related U.S. Application Data

(63) Continuation-in-part of application No. 10/771,736, filed on Feb. 4, 2004.

(60) Provisional application No. 60/444,759, filed on Feb. 4, 2003.

(51) Int. Cl.
*A61F 13/00* (2006.01)
*A61K 31/74* (2006.01)

(52) U.S. Cl. .................... 424/422; 424/78.27

(58) Field of Classification Search .................. 424/422, 424/78.27
See application file for complete search history.

(56) References Cited

U.S. PATENT DOCUMENTS

| | | | |
|---|---|---|---|
| 4,477,604 A | 10/1984 | Oechsle, III | |
| 4,570,270 A | 2/1986 | Oechsle, III | |
| 4,880,610 A | 11/1989 | Constantz | |
| RE33,161 E | 2/1990 | Brown et al. | |
| 4,902,508 A | 2/1990 | Badylak et al. | |
| RE33,221 E | 5/1990 | Brown et al. | |
| 5,034,059 A | 7/1991 | Constantz | |
| 5,047,031 A | 9/1991 | Constantz | |
| 5,053,212 A | 10/1991 | Constantz | |
| 5,129,905 A | 7/1992 | Constantz | |
| 5,149,368 A | 9/1992 | Liu et al. | |
| 5,243,038 A | 9/1993 | Ferrari et al. | |
| 5,262,166 A | 11/1993 | Liu et al. | |
| 5,263,984 A | 11/1993 | Li et al. | |
| 5,336,264 A | 8/1994 | Constanz et al. | |
| 5,462,722 A | 10/1995 | Liu et al. | |
| 5,507,810 A | 4/1996 | Prewett et al. | |
| 5,525,148 A | 6/1996 | Chow et al. | |
| 5,542,973 A | 8/1996 | Chow et al. | |
| 5,605,713 A | 2/1997 | Boltong et al. | |
| 5,607,269 A | 3/1997 | Dowd et al. | |
| 5,650,176 A | 7/1997 | Lee et al. | |
| 5,717,006 A | 2/1998 | Daculsi et al. | |
| 6,001,394 A | 12/1999 | Daculsi et al. | |
| 6,002,065 A | 12/1999 | Constantz et al. | |
| 6,127,442 A | 10/2000 | Sulzbach et al. | |
| 6,206,957 B1 | 3/2001 | Driessens et al. | |
| 6,294,187 B1 | 9/2001 | Boyce et al. | |
| 6,696,073 B2 | 2/2004 | Boyce et al. | |
| 2003/0039676 A1 | 2/2003 | Boyce et al. | |
| 2003/0144743 A1 | 7/2003 | Edwards et al. | |
| 2004/0024457 A1 | 2/2004 | Boyce et al. | |
| 2004/0146543 A1 | 7/2004 | Shimp et al. | |
| 2005/0008620 A1 | 1/2005 | Shimp et al. | |
| 2005/0008672 A1 | 1/2005 | Winterbottom et al. | |
| 2005/0013793 A1 | 1/2005 | Beckman et al. | |
| 2005/0031578 A1 | 2/2005 | Deslauriers et al. | |
| 2005/0238683 A1 | 10/2005 | Adhikari et al. | |

OTHER PUBLICATIONS

Tissue Engineering and Biodegradable Equivalents Scientific and Clinical Applications, Lewandrowski et al., Copyright 2002, Marcel Dekker, Inc., see chapter 7.*
Agrawal (eds.), et al., "Synthetic Bioabsorbable Polymers for Implants", Gorna and Gogolewski on Novel Polyurethanes, p. 39-57, Jul. 2000.
Gunatillake, et al., "Biodegradable Synthetic Polymers for Tissue Engineering", *European Cells and Materials*, 5: 1-16, 2003.
Lewandrowski, et al., "Kinetics of cortical bone demineralization: Controlled demineralization—a new method for modifying cortical bone allografts", *J. Biomed. Materials Res.*, 31: 365-72, 1996.
Morlock, et al., "Duration and frequency of every day activities in total hip patients", *J. Biomech.*, 34: 873-81, 2001.
Reddi, et al., "Biochemical sequences in the transformation of normal fibroblasts in adolescent rats", *Proc. Nat. Acad. Sci. USA*, 69: 1601-5, 1972.
Urist, "A morphogenetic matrix for differentiation of bone tissue", *Calcif. Tissue Res.*, Suppl: 98-101, 1970.
Urist, "Bone: formation by autoinduction", *Science*, 150(698); 893-9, 1965.
Weiner, "Biologically-derived or biomimetic materials such as those identified in Lowenstam HA", *On Biomineralization*, Oxford University Press, 234, 1989.
Zhang, et al., "A new peptide-based urethane polymer: synthesis, biodegradation, and potential to support cell growth in vitro", *Biomaterials*, 21: 1247-58, 2000.
Zhang, et al., "Synthesis, Biodegradability, and Biocompatibility of Lysine Diisocyanate-Glucose Tissue Engineering vol. 8 No. 5 2002 Polymers", *Tis. Eng.*, 8(5): 771-85, 2002.
Zhang, et al., "Three-dimensional biocompatible ascorbic acid-containing scaffold for bone tissue engineering," *Tissue Engineering*, 9(6): 1143-57, 2003.

\* cited by examiner

*Primary Examiner* — Raymond Henley, III

(57) ABSTRACT

Biological-based polyurethanes and methods of making the same. The polyurethanes are formed by reacting a biodegradable polyisocyanate (such as lysine diisocyanate) with an optionally hydroxylated biomolecule to form polyurethane. The polymers formed may be combined with ceramic and/or bone particles to form a composite, which may be used as an osteoimplant.

21 Claims, No Drawings

POLYURETHANES FOR OSTEOIMPLANTS

This application is a continuation-in-part of U.S. application Ser. No. 10/771,736, filed Feb. 4, 2004, which claims the benefit of U.S. Provisional Application No. 60/444,759, filed Feb. 4, 2003, the entire contents of both of which are incorporated herein by reference in its entirety.

BACKGROUND OF THE INVENTION

Vertebrate bone is a composite material composed of hydroxyapatite, collagen, and a variety of noncollagenous proteins, as well as embedded and adherent cells. Vertebrate bone can be processed into an implantable biomaterial, such as an allograft, for example, by removing the cells, leaving behind the mineral and extracellular matrix. The processed bone biomaterial can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's bone or may alternatively be processed into soft, moldable or flowable demineralized bone biomaterials that have the ability to induce a cellular healing response.

The use of bone grafts and bone substitute materials in orthopedic medicine is well known. While bone wounds can regenerate without the formation of scar tissue, fractures and other orthopedic injuries take a long time to heal, during which the bone is unable to support physiologic loading. Metal pins, screws, and meshes are frequently required to replace the mechanical functions of injured bone. However, metal is significantly stiffer than bone. Use of metal implants may result in decreased bone density around the implant site due to stress shielding. Furthermore, metal implants are permanent and unable to participate in physiological remodeling.

Following implantation, the host's own bone remodeling capabilities permit some bone grafts and certain bone substitute materials to remodel into endogenous bone that in most cases is indistinguishable from the host's own bone. In general, however, it is a limitation of allograft bone that larger allografts do not completely remodel, and residual allograft bone may persist at the graft site for many years or indefinitely, potentially acting as a stress riser and a possible fracture site. The use of bone grafts is further limited by the availability of tissue with the appropriate shape and size, as well as the desired mechanical strength and degradation rate.

U.S. Pat. No. 6,294,187, the contents of which are incorporated herein by reference, describes methods for preparing composites including allogenic bone for use in load bearing orthopedic applications. It is desirable to increase the strength of bone-reinforced composites by increasing the strength of the matrix material while retaining the resorbable properties of the matrix. Furthermore, there is a need for a novel resorbable polymer capable of synergistically interacting with bone to make a true composite having mechanical characteristics of both bone and polymer. There is also a need to develop resorbable polymers for the production of bone/polymer composites where the polymer itself contributes to osteointegration and remodeling of the composite. It is also desirable to develop implants that do not elicit undesirable immune responses from the recipient. There is also a need to provide composite grafts of suitable shape and size that maximize the utility of the graft tissue.

SUMMARY OF THE INVENTION

In one embodiment, the invention is a polyurethane composite including a polyurethane formed by reaction of a polyisocyanate with a hydroxylated or aminated material to form a polyurethane polymer. The composite includes an included material including one or more of a biomolecule, extracellular matrix component, bioactive agent, small molecule, tissue-derived material, inorganic ceramic, bone substitute, and modified forms of these. The included material may include a composite including one or more of an inorganic ceramic and a bone-derived material and one or more of bovine serum albumin, collagen, an extracellular matrix component, a synthetic polymer, and a naturally derived polymer. Modified forms may have an increased surface concentration of hydroxyl or amine groups with respect to the unmodified material. The included material may be the hydroxylated or aminated material. The tissue-derived material may include bone, demineralized bone, deorganified bone, or tissue derived from tendon, ligament, cartilage, endodermis, small intestine, mucosa, skin, or muscle. At least a portion of the bone or bone substitute may be lightly demineralized. The biomolecule may be selected from phospholipids, fatty acids, cholesterols, polysaccharides, lecithin, starches, collagen, and combinations and modified forms of the above. The included material may be selected from lectins, growth factors, immunosuppressives, chemoattractants, antibiotics, and anticoagulants. The polyurethane may have a wet compressive strength that exceeds the wet compressive strength of the polyurethane alone. The polyurethane composite may degrade at a rate sufficient to permit generation of new tissue at an in vivo implantation site.

In another embodiment, the invention is biodegradable polyurethane formed by reaction of a polyisocyanate with optionally hydroxylated biomolecules to form a polyurethane polymer. The optionally hydroxylated biomolecules include one or more of polysaccharides and starches and one or more of lipids and phospholipids. An included material may be combined with the polyurethane, for example, a tissue-derived material, an inorganic ceramic, a bone substitute material, modified forms of the above, or any combination. The included material may itself include a composite.

In another embodiment, the invention is a non-biodegradable polyurethane formed by reaction of a polyisocyanate with optionally hydroxylated biomolecules to form a polyurethane polymer. The optionally hydroxylated biomolecules include one or more of polysaccharides and starches.

In another aspect, the invention is a method of making a polyurethane composite. The method includes reacting a polyisocyanate with a hydroxylated or aminated material in the presence of an included material to form a polyurethane polymer matrix having particles of the included material embedded therein. The included material includes a biomolecule, extracellular matrix component, bioactive agent, small molecule, tissue-derived material, inorganic ceramic, bone substitute, modified forms of the above, or a mixture of any of these. Reacting may include reacting the polyisocyanate and the aminated or hydroxylated material to form a prepolymer, mixing the prepolymer with the included material to form a precomposite, and reacting the precomposite to form the polyurethane composite. Reacting the precomposite may include cross-linking the prepolymer, reacting for a time period from about one minute to about four hours, or exposing the polyisocyanate and the hydroxylated or aminated material to a catalyst. The catalyst may include a material selected from mild bases, strong bases, sodium hydroxide, sodium acetate, tin, and triethylene diamine 1,4-diaza(2,2,2) bicyclooctane. The method may further include increasing the cross-link density of the polyurethane polymer matrix.

DEFINITIONS

As used herein, "bioactive agents" is used to refer to compounds or entities that alter, inhibit, activate, or otherwise affect biological or chemical events. For example, bioactive agents may include, but are not limited to, bone growth enhancers such as but not limited to bone morphogenetic proteins, anti-AIDS substances, anti-cancer substances, antibiotics, immunosuppressants (e.g., cyclosporine), anti-viral substances, enzyme inhibitors, neurotoxins, opioids, hypnotics, anti-histamines, lubricants, tranquilizers, anti-convulsants, muscle relaxants and anti-Parkinson substances, antispasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, imaging agents, specific targeting agents, neurotransmitters, proteins, cell response modifiers, and vaccines. In a certain preferred embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formulary-20, published by the United States Pharmcopeial Convention, Inc., Rockville Md., 2001, and the "Pharmazeutische Wirkstoffe," edited by Von Keemann et al., Stuttgart/New York, 1987, all of which are incorporated herein by reference.

The term "biocompatible," as used herein, is intended to describe materials that, upon administration in vivo, do not induce undesirable long term effects.

As used herein, "biodegradable," "bioerodable," or "resorbable" materials are materials that degrade under physiological conditions to form a product that can be metabolized or excreted. Biodegradable materials are not necessarily hydrolytically degradable and may require enzymatic action to fully degrade. Biodegradable materials also include materials that are broken down within cells.

The term "biomolecules," as used herein, refers to classes of molecules (e.g., proteins, amino acids, peptides, polynucleotides, nucleotides, carbohydrates, sugars, lipids, nucleoproteins, glycoproteins, lipoproteins, steroids, etc.) that are commonly found in cells and tissues, whether the molecules themselves are naturally-occurring or artificially created (e.g., by synthetic or recombinant methods). For example, biomolecules include, but are not limited to, enzymes, receptors, collagen, neurotransmitters, hormones, cytokines, cell response modifiers such as growth factors and chemotactic factors, antibodies, vaccines, haptens, toxins, interferons, ribozymes, anti-sense agents, plasmids, DNA, RNA, extracellular matrix (ECM) components, and synthetic analogs of ECM components.

As used herein, the term "composite" refers to a mixture of two or more different materials. In one embodiment, the two materials are a polymer and an additional material. The additional material may include several materials having different compositions, sizes, shapes, or other characteristics. While the polymer may act as a binder to hold together particles, fibers, or fragments of additional material(s), it is not required that the polymer be fully interconnected throughout the composite; neither is it assumed that the additional material is or is not interconnected throughout the composite.

"Deorganified", as herein applied to matrices, particles, etc., refers to bone or cartilage matrices, particles, etc., that were subjected to a process that removes at least part of their original organic content. In some embodiments, at least 1%, 10%, 20%, 30%, 40%, 50%, 60%, 70%, 80%, 90%, or 99% of the organic content of the starting material is removed. Deorganified bone from which substantially all the organic components have been removed is termed "anorganic."

"Growth Factors": As used herein, "growth factors" are chemicals that regulate cellular metabolic processes, including but not limited to differentiation, proliferation, synthesis of various cellular products, and other metabolic activities. Growth factors may include several families of chemicals, including but not limited to cytokines, eicosanoids, and differentiation factors.such as platelet-derived growth factor (PDGF). Other factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein. Other growth factors are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenic proteins including all BMPs, including but not limited to BMP-2, BMP-4, and BMP-7.

The term "osteogenic," as applied to the osteoimplant of this invention, shall be understood as referring to the ability of the osteoimplant to enhance or accelerate the ingrowth of new bone tissue by one or more mechanisms such as osteogenesis, osteoconduction and/or osteoinduction.

The term "polyisocyanate," as that term is used herein, encompasses any chemical structure comprising two or more cyanate groups. A "diisocyanate," as used herein, is a subset of the class of polyisocyanates, a chemical structure containing exactly two cyanate (—CN) groups. Similarly, a "polyol" contains two or more alcohol (—OH) groups, while a "diol" contains exactly two alcohol groups, and a "polyamine" contains two or more primary amine groups.

"Polynucleotide," "nucleic acid," or "oligonucleotide": The terms "polynucleotide," "nucleic acid," or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Polypeptide", "peptide", or "protein": According to the present invention, a "polypeptide," "peptide," or "protein" comprises a string of at least two amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide," "carbohydrate," "oligosaccharide," or "starch" refer to a polymer of sugars. The terms "polysaccharide" and "carbohydrate" may be used interchangeably to mean a sugar polymer of any length. "Oligosaccharide" generally refers to a relatively low molecular weight polymer, while "starch" typically refers to a higher molecular weight polymer. The polymer may include natural sugars (e.g., glucose, fructose, galactose, mannose, arabinose, ribose, and xylose) and/or modified sugars (e.g., 2'-fluororibose, 2'-deoxyribose, and hexose). Polysaccharides may or may not be crosslinked.

The term "polyurethane," as used herein, is intended to include all polymers incorporating more than one urethane group (—NH—CO—O—) or more than one area group (—NH—CO—NH—) in the polymer backbone. Polymers containing only urea linkages, although technically termed polyureas, are also referred to herein as polyurethanes.

The term "shaped," as applied to the osteoimplant herein, refers to a determined or regular form or configuration, in contrast to an indeterminate or vague form or configuration (as in the case of a lump or other solid mass of no special form) and is characteristic of such materials as sheet, plate, particle, sphere, hemisphere strand, coiled strand, capillary network, film, fiber, mesh, disk, cone, portion of a cone, pin, screw, tube, cup, tooth, tooth root, strut, wedge, portion of wedge, cylinder, threaded cylinder, rod, hinge, rivet, anchor, spheroid, ellipsoid, oblate spheroid, prolate ellipsoid, hyperbolic paraboloid, and the like.

"Small molecule": As used herein, the term "small molecule" is used to refer to molecules, whether naturally-occurring or artificially created (e.g., via chemical synthesis), that have a relatively low molecular weight. Typically, small molecules have a molecular weight of less than about 5000 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present invention.

As utilized herein, the phrase "superficially demineralized" as applied to bone particles refers to bone particles possessing at least about 90 weight percent of their original inorganic mineral content. The phrase "partially demineralized" as applied to the bone particles refers to bone particles possessing from about 8 to about 90 weight percent of their original inorganic mineral content, and the phrase "fully demineralized" as applied to the bone particles refers to bone particles possessing less than about 8, for example, less than about 1, weight percent of their original inorganic mineral content. The unmodified term "demineralized" as applied to the bone particles is intended to cover any one or combination of the foregoing types of demineralized bone particles.

Unless otherwise specified, all material proportions used herein are in weight percent.

The phrase "wet compressive strength," as utilized herein, refers to the compressive strength of the osteoimplant after the osteoimplant has been immersed in simulated body fluid (SBF) for a minimum of 12 hours. Compressive strength is a well-known measurement of mechanical strength and is measured using the procedure described herein.

DETAILED DESCRIPTION OF CERTAIN PREFERRED EMBODIMENTS

In one embodiment, a polyurethane composite includes a polyurethane formed by reaction of a polyisocyanate with a hydroxylated or aminated material. The composite includes and included material, e.g., a biomolecule, extracellular matrix component, bioactive agent, small molecule, tissue-derived material, inorganic ceramic, bone substitute, a composite of an inorganic ceramic with one or more of a tissue-derived material, extracellular matrix material, and bovine serum albumin, or a mixture thereof.

Components of a Polyurethane Composite

Polyurethanes are often formed by the reaction of a polyisocyanate (such as a diisocyanate) with a polyol (such as a diol):

HO—R$_1$—OH + OCN—R$_2$—NCO ⟶

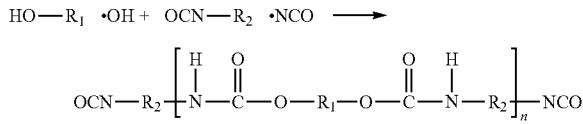

Polyurethanes may be straight chains or branched, and may have high or low molecular weights. Polyurethanes may also contain urea linkages formed by the reaction of an isocyanate with an amine. In an alternative embodiment, polyurethanes are formed by reacting a polyol with an excess of polyisocyanate to form a macropolyisocyanate prepolymer, following which the prepolymer is reacted with a second polyol or polyamine to form the polyurethane:

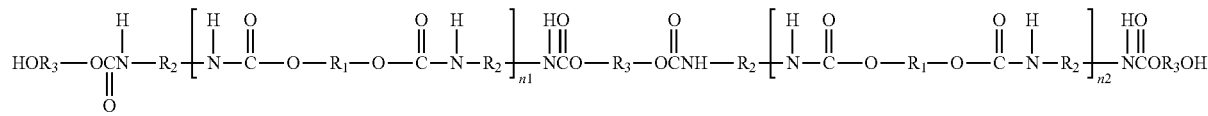

The $R_1$, $R_2$, and $R_3$ groups provide great flexibility in tailoring the mechanical and chemical properties of polyurethanes, which may be made rigid, soft, plastic, and/or elastomeric by selection of appropriate functional groups. The use of R groups having different types of chemical linkages creates regions of the polyurethane that are more and less flexible. For example, aromatic and polyaromatic R groups increase the rigidity of that segment of the polymer, while alkane and polyol chains are relatively flexible. The mixture of rigid, or hard, with flexible, or soft, segments in a polyurethane results in a strong, tough, elastomeric material. The ratio of hard and soft segments may be adjusted to optimize the mechanical properties of the composite.

Exemplary polyisocyanates for use in embodiments of the invention include but are not limited to 1,5-naphthalene diisocyanate, isophone diisocyanate, 3,3-bitoluene diisocyanate, cyclohexyl diisocyanate, 2,6-tolylene diisocyanate, methylene bis (p-cyclohexyl isocyanate), toluene diisocyanate, methylene bis (p-phenyl isocyanate), hexamethylene diisocyanate, 1,4-butanediisocyanate, 2,2,4-triethylhexamethylene diisocyanate, 2,2,4-trimethylhexamethylene diisocyanate, 2,6-diisocyanato methyl caproate, arginine diisocyanate, asparagine diisocyanate, proline diisocyanate, glutamine diisocyanate, isocyanurate polyisocyanates, uretdione polyisocyanate, lysine diisocyanate, lysine ethyl ester diisocyanate, lysine methyl ester diisocyanate, and derivatives of these described below. Zhang et al. have synthesized a lysine diisocyanate ethyl ester, $OCN(CH_2)_4CH\ [NCO][COOC_2H_5]$, which they have found to be biocompatible (see Zhang, et al., "A new peptide-based urethane polymer: synthesis, biodegradation, and potential to support cell growth in vitro," *Biomaterials* 21: 1247-1258 (2000), and Zhang, et al., "Synthesis, Biodegradability, and Biocompatibility of Lysine Diisocyanate-Glucose Polymers," *Tiss. Eng.*, 8(5): 771-785 (2002), both of which are incorporated herein by reference). In some embodiments, the polyisocyanate is resorbable.

Exemplary polyols and polyamines include but are not limited to degradable polyesters such as polylactide and polyglycolide and their copolymers, amino acid oligomers including hydroxylated or aminated residues, polyether polyols, e.g., polyethylene glycol and polypropylene glycol, polytetramethylene ether glycol, hydroxylated or aminated hydrocarbons, hydroxybutyl or butylamine terminated polydimethylsiloxanes, polydimethylsiloxane glycol, polycaprolactones, polyhydroxybutyrate, polyhydroyvalerate, polycarbonates, tyrosine-based polycarbonates, polytetramethylene oxide, myoinisitol (a pentahydroxy sugar), poly(glycolide-co-γ-caprolactone), glycerol, ethylene glycol copolymers, DIOREZ™ (a commercially available polyester polyol), PLURONICS™ polymers, polyethylene oxide, polypropylene oxide, hydroxyl or amine terminated poly(1,4-butadiene), hydrogenated or aminated polybutadiene, ethylene diamine, phenylalanine-based esters (see U.S. Pat. No. 6,221, 997), adipic acid, hydroxyl or amine terminated polyisobutylene, polyhexamethylene carbonate glycol, amine-terminated polyethers; polyester polyols (such as polybutylene adipate, polyethylene adipate, polytetramethylene adipate caprolactone polyesters, castor oil); and polycarbonates (such as poly(1,6-hexanediol) carbonate), and copolymers of any of these. In some embodiments, the polyol or polyamine has a molecular weight of about 400 to about 5000.

Exemplary chain extenders include but are not limited to 1,4-cyclohexane dimethanol, polyols of polyhydroxybutyrate and polyhydroxyvalerate, polylactide, polyglycolide, poly(lactide-co-glycolide), biocompatible diester diols and diurea diols, 1,4-butanediol, ethylene diamine, 4,4'-methylene bis (2-chloroaniline), ethylene glycol, 3-hexyne-2,5-diol, 2-amino-1-butanol, and hexanediol. One skilled in the art will recognize that other aromatic and aliphatic diols and diamines may also be employed as chain extenders. The use of biologically derived materials is discussed below.

In some embodiments, $R_1$, $R_2$, or $R_3$ may include alkyl, aryl, heterocycles, cycloalkyl, aromatic heterocycles, multicycloalkyl, hydroxyl, ester, ether, carboxylic acid, amino, alkylamino, dialkylamino, trialkylamino, amido, alkoxy, or ureido groups. Alternatively or in addition, $R_1$, $R_2$, or $R_3$ may also include branches or substituents including alkyl, aryl, heterocycles, cycloalkyl, aromatic heterocycles, multicycloalkyl, hydroxyl, ester, ether, halide, carboxylic acid, amino, alkylamino, dialkylamino, trialkylamino, amido, carbamoyl, thioether, thiol, alkoxy, or ureido groups. Exemplary groups for use as $R_1$, $R_2$, or $R_3$ also include bioactive agents, biomolecules, and small molecules. Appropriate polyurethanes also include those disclosed in U.S. Patent Publication No. 2005/0013793, the contents of which are incorporated herein by reference.

In some embodiments, polyurethane composites are formed by reacting an appropriate polyisocyanate crosslinker (e.g., a diisocyanate) or macropolyisocyanate prepolymer with an aminated or hydroxylated material to form composites which may have osteogenic and/or osteoinductive properties. Of course, the material may have both amine and hydroxyl groups. The composites also incorporate an included material, for example, a biomolecule, extracellular matrix component, bioactive agent, small molecule, bone, bone substitute, tissue derived material, inorganic ceramic, or a mixture of these. Details of traditional polyurethane synthesis can be found, for example, in Lamba, et al., *Polyurethanes in Biomedical Applications*, CRC Press, 1998, which is incorporated herein by reference, and particularly in Chapter 2 of the above reference. The hydroxylated or aminated material may serve as a polyol/polyamine in a macropolyisocyanate, as a chain extender, or as any of $R_1$, $R_2$, or $R_3$.

Naturally derived materials may also be used as polyols or polyamines and may serve as part of the macropolyisocyanate, the chain extender, or both. In one embodiment, the hydroxylated or aminated material is a biomolecule, for example, a lipid (e.g., phospholipid, lecithin, fatty acid, triglyceride, or cholesterol) or polysaccharide (e.g., oligosaccharide or amylase-resistant starches). A biomolecule for use according to the techniques of the invention may be hydroxylated by any method known to those skilled in the art if it does not already possess sufficient reactive groups to carry out a reaction. For example, lipids, including phospholipids, mono-, di-, and triglycerides, fatty acids, and cholesterols may require addition of hydroxyl or amine groups in order to carry out the polymerization reaction. In contrast, many polysaccharides already have sufficient hydroxyl groups to polymerize readily into a highly cross-linked polymer.

The hydroxylated or aminated material may also include intact extracellular matrix (ECM), its components, alone or in combination, or modified or synthetic versions thereof. These materials may be treated to increase the concentration of hydroxyl and/or amino groups, especially the surface concentration of these groups. For example, collagen may be decross-linked or treated with lysyl oxidase. Lysyl oxidase converts the terminal amino groups of lysine to aldehydes, which may then be reduced. Alternatively or in addition, the biomolecule, or ECM component, or tissue may be aminated. The amino groups will be incorporated into the polymer through a urea linkage. Of course, many ECM derived materials already contain primary amino groups. Exemplary extracellular matrix components suitable for use with the invention include but are not limited to collagen, laminin, elastin, proteoglycans, reticulin, fibronectin, vitronectin, glycosaminoglycans, and other basement membrane components. Various types of collagen (e.g., collagen Type I, collagen Type II, collagen Type IV, etc., as well as collagen derived or denatured materials such as gelatin) are suitable for use with the invention. Collagens may be used in fiber, gel, or other forms. Sources for extracellular matrix components include, but are not limited to, skin, tendon, intestine and dura mater obtained from animals, transgenic animals and humans. Extracellular matrix components are also commercially available, for example, from Becton Dickinson. Collagenous tissue can also be obtained by genetically engineering microorganisms to express collagen as described, e.g., in U.S. Pat. No. 5,243,038, the entire contents of which are incorporated herein by reference. Procedures for obtaining and purifying collagen are well known in the art and typically involve acid or enzyme extraction as described, e.g., in U.S. Pat. No. 5,263,984, the contents of which are incorporated by reference herein. Exemplary synthetic ECM analogs include RGD-containing peptides, silk-elastin polymers produced by Protein Polymer Technologies (San Diego, Calif.) and BioSteel™, a recombinant spider silk produced by Nexia Biotechnologies (Vaudrevil-Dorion, QC, Canada). Various types of collagen (e.g., collagen Type I, collagen Type II, collagen Type IV) are also suitable for use with embodiments of the invention.

Tissues, including but not limited to xenograft, allograft, or autograft tissues, including non-bony tissues and bone-derived tissues, may be used with the invention. The preparation of bone pieces and particles for incorporation into composites is discussed below. Non-bony tissues suitable for use with the invention include connective tissue such as tendon, ligament, cartilage, endodermis, small intestinal submucosa, skin, and muscle. The tissues may be excised and cut into a plurality of elongated fragments or particles employing methods known in the art. Reduction of the antigenicity of allogeneic and xenogeneic tissue can be achieved by treating the tissues with various chemical agents, e.g., extraction agents such as monoglycerides, diglycerides, triglycerides, dimethyl formamide, etc., as described, e.g., in U.S. Pat. No. 5,507,810, the contents of which are incorporated by reference herein. Small intestine submucosa tissue can be obtained and processed as described in U.S. Pat. No. 4,902,508, the contents of which are incorporated by reference herein. In summary, intestinal tissue is abraded to remove the outer layers, including both the tunica serosa and the tunica muscularis and the inner layers, including at least the luminal portion of the tunica mucosa. The resulting material is a whitish, translucent tube of tissue approximately 0.1 mm thick, typically consisting of the tunica submucosa with the attached lamina muscularis mucosa and stratum compactum. The tissue may be rinsed in 10% neomycin sulfate before use. Tissues may be modified by demineralization, amination, or hydroxylation before use. For example, lysine groups may be modified with lysyl oxidase as described above.

Ceramics, including calcium phosphate materials and bone substitute materials, may also be exploited for use as particulate inclusions or as the hydroxylated or aminated material. Exemplary inorganic ceramics for use with the invention include calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, and BIOGLASS™, a calcium phosphate silica glass available from U.S. Biomaterials Corporation. Substituted CaP phases are also contemplated for use with the invention, including but not limited to fluorapatite, chlorapatite, Mg-substituted tricalcium phosphate, and carbonate hydroxyapatite. Additional calcium phosphate phases suitable for use with the invention include those disclosed in U.S. Pat. Nos. RE 33,161 and RE 33,221 to Brown et al.; U.S. Pat. Nos. 4,880,610; 5,034,059; 5,047,031; 5,053,212; 5,129,905; 5,336,264; and 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., U.S. Pat. No. 5,650,176 to Lee et al., and U.S. Pat. No. 6,206,957 to Driessens et al, and biologically-derived or biomimetic materials such as those identified in Lowenstam H A, Weiner S, *On Biomineralization*, Oxford University Press, 1989, incorporated herein by reference. The composite may contain between about 5 and 80% bone-derived or other ceramic material, for example, between about 60 and about 75%.

In another embodiment, a composite material may be reacted with a macropolyisocyanate to form a polyurethane composite. For example, inorganic ceramics such as those described above or bone-derived materials may be combined with proteins such as BSA, collagen, or other extracellular matrix components such as those described above to form a composite. Alternatively or in addition, inorganic ceramics or bone-derived materials may be combined with synthetic or naturally-derived polymers to form a composite using the techniques described in our co-pending applications Ser. No. 10/735,135, filed Dec. 12, 2003, Ser. No. 10/681,651, filed Oct. 8, 2003, and Ser. No. 10/639,912, filed Aug. 12, 2003, the contents of all of which are incorporated herein by reference. These composites may be lightly demineralized as described below to expose the organic material at the surface of the composite before they are formed into polyurethane composites according to the teachings of the invention.

Particulate materials for use with an embodiment of the invention may be modified to increase the concentration of amino or hydroxyl groups at their surfaces using the techniques described elsewhere herein. Particulate materials may also be rendered more reactive through treatment with silane coupling reagents, such as those described in our co-pending application, published as U.S. Patent Publication No. 20050008620, the entire contents of which are incorporated herein by reference. Coupling agents may be used to link polyisocyanate, polyamine, or polyol molecules to the particle or simply to attach individual amine, hydroxyl or isocyanate groups. The linked molecules may be monomeric or oligomeric.

When the hydroxylated or aminated material is difunctional, reaction with a diisocyanate generally produces a polyurethane with minimal crosslinking. Such polymers are generally thermoplastic and readily deformable and may be subjected to strain-induced crystallization for hardening. In contrast, if at least some reactants include at least three active groups participating in the reaction, then the polymer will generally be heavily cross-linked. Such polymers are often thermosets and tend to be harder than polymers with low cross-linking. In addition, their mechanical properties tend to be less dependent on how they are processed, which may render them more machinable. Cross-linking may also be controlled through the choice of catalyst. Exemplary catalysts include mild bases, strong bases, sodium hydroxide, sodium acetate, tin, and triethylene diamine-1,4-diaza(2,2,2)bicyclooctane. Tin and other metal carboxylates promote branching and crosslinking during polyurethane formation. The stoichiometry and temperature of the reaction may also be adjusted to control the extent of crosslinking.

Because the reaction process combines an isocyanate with a biomolecule or other biological or biocompatible material, many possible breakdown products of the polymer according to certain embodiments are themselves resorbable. In one embodiment, byproducts of enzymatic degradation, dissolution, bioerosion, or other degradative processes are biocompatible. These byproducts may be utilized in or may be metabolites of any cellular metabolic pathway, such as but not limited to cellular respiration, glycolysis, fermentation, or the tricarboxylic acid cycle. In one embodiment, the polyurethanes of the invention are themselves enzymatically degradable, bioerodable, hydrolyzable, and/or bioabsorbable. Thus, when an osteoimplant is formed from the materials of the invention, it can be slowly replaced by the ingrowth of natural bone as the implant degrades. This process of osteogenesis may be accelerated, for example, by the addition of bioactive agents. Such bioactive agents may be incorporated into the polymer structure, either as backbone elements or as side groups, or they may be present as solutes in the solid polymer or as non-covalently bonded attachments. In any case, they may be gradually released as the polyurethane degrades. The rate of release may be tailored by modifying the attachment or incorporation of the bioactive agents into the polymer. Bioactive agents that may be used include not only agents having osteogenic properties, but also agents having other biological properties such as immunosuppression and chemoattraction. Exemplary bioactive agents include bone stimulating peptides such as RGD, bone morphogenic proteins, and other growth factors. Lectins are a class of particular interest for incorporation into the present polymers, especially when the polymers comprise carbohydrates, which bond readily to lectins.

For certain applications, it may be desirable to create foamed polyurethane, rather than solid polyurethane. While typical foaming agents such as hydrochlorofluorocarbons, hydrofluorocarbons, and pentanes may not be biocompatible for many systems, other biocompatible agents may be used. For example, Zhang et al. have found that water may be an adequate foaming agent for a lysine diisocyanate/PEG/glycerol polyurethane (see Zhang, et al., "Three-dimensional biocompatible ascorbic acid-containing scaffold for bone tissue engineering," supra) and may also be used to cause foaming in other polyurethanes. Other foaming agents include dry ice or other agents that release carbon dioxide or other gases into the composite. Alternatively, or in addition, salts may be mixed in with the reagents and then dissolved after polymerization to leave behind small voids.

Whether foamed or solid, polyurethanes may be formed with an additional, included material. Exemplary included materials include but are not limited to bone-derived tissue, non-bone derived tissue, and ceramics and bone substitute materials. In some embodiments, settable osteogenic materials (e.g. α-BSM, available from ETEX Corp, Cambridge, Mass., Norian SRS, (Skeletal Repair System) available from Norian Corp, Cupertino, Calif., or Dynaflex, available from Citagenix) is included in the polyurethane composite. These materials may bond strongly to the isocyanates used in forming the polymer, since they contain or may be modified to contain significant numbers of active hydroxyl groups. Thus, it may be preferred in some embodiments to first mix the included material with the hydroxylated or aminated material, before addition of the isocyanate. Nevertheless, it is also within the scope of the invention to mix the additional material into already-combined hydroxylated or aminated material and isocyanate, or to combine all three components simultaneously. The amount of included material in the composite will vary depending on the desired application, and practically any amount of material, for example, at least 10, at least 30, at least 50, or at least 70% of the composite may be formed from the included material.

Of course, the included material may serve as the hydroxylated or aminated material. That is, materials such as biomolecules, extracellular matrix components, bioactive agents, small molecules, tissue-derived materials, inorganic ceramics, bone substitutes, and composites, such as those described above, of inorganic ceramics or bone derived materials with synthetic or naturally derived materials, extracellular matrix material, and bovine serum albumin may react with the polyisocyanate to form a polyurethane composite. In some embodiments, it may be desired to form a prepolymer of isocyanate-terminated polyurethane oligomers and react these with the included material to form the composite to add flexibility to the polymer matrix.

Preparation of Bone for Incorporation into Composites

In one embodiment, the bone particles are produced from fully mineralized human cortical bone. Bone particles for use in the composites of the invention may also be obtained from cortical, cancellous, and/or corticocancellous bone which may be of autogenous, allogenic and/or xenogeneic origin and may or may not contain cells and/or cellular components. Porcine and bovine bone are particularly advantageous types of xenogeneic bone tissue that may be used individually or in combination as sources for the bone particles. Bone particles for use in the composites of the invention may be any shape including, for example, irregular particulates, plates, fibers, helices and the like. Exemplary fibers may have a length between 0.05 and 500 mm, for example, between 5 and 100 mm, a thickness between 0.01 and 2 mm, for example, between 0.05 and 1 mm, and a width between 0.1 and 20 mm, for example, between 2 and 5 mm. As described herein, bone fibers are particles having at least one aspect ratio of 2:1 or greater. In some embodiments, bone fibers may have a ratio of width to length of at least 5:1, 10:1, 15:1, 25:1, 50:1, 200:1, or 500:1.

Bone particles may be obtained by milling or shaving sequential surfaces of an entire bone or relatively large section of bone. A non-helical, four fluted end mill may be used to produce fibers having the same orientation as the milled block. Such a mill has straight grooves, or flutes, similar to a reamer, rather than helical flutes resembling a drill bit. During the milling process, the bone may be oriented such that the natural growth pattern (along the long axis) of the piece being milled is along the long axis of the end mill of the milling machine. Multiple passes of the non-helical end mill over the bone results in bone particles having a long axis parallel to that of the original bone (FIGS. 1, 2). Bone particles and fibers with different sizes, dimensions, and aspect ratios may be obtained by adjusting the milling parameters, including sweep speed, bit engagement, rpm, cut depth, etc.

Elongated bone fibers may also be produced using the bone processing mill described in commonly assigned U.S. Pat. No. 5,607,269, the entire contents of which are incorporated herein by reference. Use of this bone mill results in the production of long, thin strips which quickly curl lengthwise to provide helical, tube-like bone particles. A great variety of particle shapes (curled fiber, uncurled fiber, ribbon, ship, short fiber, etc.) may be achieved by varying the speed, feed, attack depth, engagement length and bit design. Elongated bone particles may be graded into different sizes to reduce or eliminate any less desirable size(s) of particles that may be present. In overall appearance, particles produced using this mill may be described as filaments, fibers, threads, slender or narrow strips, etc. In alternative embodiments, bone fibers and particles may be produced by chipping, rolling, fracturing with liquid nitrogen, chiseling or planeing, broaching, cutting, or splitting along the axis (e.g., as wood is split with a wedge).

The bone fibers may be sieved into different diameter sizes to eliminate any less desirably sized fibers or more evenly dimensioned particles that may be present. In one embodiment, fibers collected from the milling machine may be lyophilized and manually sieved into a range of 3-6 mm in length. Fiber length may be independent of cross-sectional dimension and may be modified by adjusting the bit engagement length, the length of the bit in contact with the bone during the milling operation. Fibers may be an inch long or greater and may be as short as desired, depending on the desired aspect ratio. Fibers less than 50 µm long may increase the likelihood of inflammation depending on the tissues and how the implant degrades. In some instances, particles or fibers of this size may be advantageously included to promote faster bone healing by eliciting a mild inflammatory response. Larger fibers may be further broken into smaller fibers by manually rolling them between the thumb and fingers or by an equivalent automated method and then sieved again to select the proper size fibers. Alternatively, fibers may be broken into smaller fibers by pressing or rolling. The resulting fibers may have an aspect ratio of 5:1 to 10:1. Broader or narrower fibers may be obtained by changing sieve grate sizes.

Larger bone pieces may also be incorporated into composites produced using the techniques of the invention. For example, fragments or pieces of bone may be employed. Exemplary bone pieces include portions of the diaphysis or metaphysis of the long bones, e.g., femur, tibia, ulna, humerus, fibula, and radius, the phalanges or portions thereof, or large pieces cut from bones such as the pelvis or jaw. Such pieces may include transverse or longitudinal sections, portions of sections, or arbitrarily shaped bits. Alternatively or in addition, bone may be cut into shapes that are used for orthopedic implants or assembled to form an implant before being combined with monomer or polymer. Exemplary shapes are shown in FIG. 1.

The bone particles or pieces are optionally demineralized in accordance with known and conventional procedures in order to reduce their inorganic mineral content. Demineralization methods remove the inorganic mineral component of bone, for example by employing acid solutions. Such methods are well known in the art, see for example, Reddi, et al., *Proc. Nat. Acad. Sci.,* 1972, 69:1601-1605, the contents of which are incorporated herein by reference. The strength of the acid solution, the shape of the bone particles and the duration of the demineralization treatment will determine the extent of demineralization. Reference in this regard may be made to Lewandrowski, et al., *J. Biomed. Mater. Res.,* 1996, 31: 365-372, the contents of which are also incorporated herein by reference. Bone particles may also be partially demineralized. For example, bone particles may be demineralized to a depth greater than 100 µm, for example, between 100 and 5000 µm, between 150 µm and 2000 µm, or between 200 and 1000 µm.

In an exemplary demineralization procedure, the bone particles are subjected to an optional defatting/disinfecting step, followed by an acid demineralization step. An exemplary defatting/disinfectant solution is an aqueous solution of ethanol. Ordinarily, at least about 10 to about 40 percent by weight of water (i.e., about 60 to about 90 weight percent of defatting agent such as alcohol) is present in the defatting/disinfecting solution to optimize lipid removal and disinfection and processing time. An exemplary concentration range of the defatting solution is from about 60 to about 85 weight percent alcohol, for example, about 70 weight percent alcohol. Following defatting, the bone particles are immersed in acid over time to effect their demineralization. The acid may also disinfect the bone by killing viruses, vegetative microorganisms, and/or spores. Acids that may be employed in this step include inorganic acids such as hydrochloric acid and organic acids such as peracetic acid. Alternative acids are well known to those skilled in the art. After acid treatment, the demineralized bone particles are rinsed with sterile water to remove residual amounts of acid and raise the pH. The bone particles may be dried, for example, by lyophilization, before being incorporated into the composite. The bone particles may be stored under aseptic conditions until they are used or sterilized using known methods shortly before incorporation into the composite. Additional demineralization methods are well known to those skilled in the art, for example, the method cited in Urist M R, A morphogenetic matrix for differentiation of bone tissue, *Calcif Tissue Res.* 1970; Suppl:98-101 and Urist M R, Bone: formation by autoinduction, *Science.* 1965 Nov. 12,; 150(698):893-9, the contents of both of which are incorporated herein by reference.

In an alternative embodiment, surfaces of bone particles may be lightly demineralized according to the procedures in our commonly owned U.S. patent application Ser. No. 10/285,715, published as U.S. Patent Publication No. 20030144743, the entire contents of which are incorporated herein by reference. Even minimal demineralization, for example, of less than 5% removal of the inorganic phase, increases the hydroxylation of bone fibers and the surface concentration of amine groups. Demineralization may be so minimal, for example, less than 1%, that the removal of the calcium phosphate phase is almost undetectable. Rather, the enhanced surface concentration of reactive groups defines the extent of demineralization. This may be measured, for example, by titrating the reactive groups. In one embodiment, in a polymerization reaction that utilizes the exposed allograft surfaces to initiate a reaction, the amount of unreacted monomer remaining may be used to estimate reactivity of the surfaces. Surface reactivity may be assessed by a surrogate mechanical test, such as a peel test of a treated coupon of bone adhering to a polymer. Alternatively or in addition, a portion of the surface of the bone particles may be so demineralized.

Mixtures or combinations of one or more of the above types of bone particles can be employed. For example, one or more of the foregoing types of demineralized bone particles can be employed in combination with nondemineralized bone particles, i.e., bone particles that have not been subjected to a demineralization process. Anorganic bone, bone from which at least a portion of the organic content has been removed, may also be employed, either alone or in combination with other bone derived or non-bone derived materials. The demineralized bone particles may behave as short fibers in the composite, acting to increase fracture toughness. The nondemineralized bone particles may behave as ceramic inclusions, increasing the compressive strength of the composite. Nondemineralized bone is itself a fiber-reinforced composite, which may increase the bending and tensile stress the composite can withstand before the bone particles break. Superficial demineralization produces particles containing a mineralized core. Particles of this type may behave as nondemineralized particles in the composite, depending on the degree of demineralization. Minimally demineralized bone and other partially demineralized bone pieces may be combined to form composite sandwiches having carefully tailored mechanical properties. Slabs of bone demineralized to the same or different degrees may be sandwiched using a polyurethane using the techniques provided by the invention. Multi-layered structures may also be produced. Bone may also be processed to remove a portion of the organic content (e.g., deorganified bone), or commercially available products such as BIO-OSS™ available from Osteohealth, may be used.

Preparation of Polyurethane Composites

The hydroxylated or aminated material, any included material, and the polyisocyanate or macropolyisocyanate may be combined using standard composite processing techniques. The techniques described in our co-pending U.S. patent applications Ser. No. 10/639,912, filed Aug. 12, 2003, and Ser. No. 10/735,135, filed Dec. 12, 2003, and those disclosed in our co-pending application entitled "Injectable and Settable Bone Substitute Material", filed on even date herewith, may also be used to prepare the polyurethane and implant it into a tissue site.

For example, the components may be combined and injection molded, injected, extruded, laminated, sheet formed, foamed, or processed using other techniques known to those skilled in the art. Reaction injection molding methods, in which a polyisocyanate and a polyol are separately charged into a mold under precisely defined conditions, may be employed. For example, the included material may be added to one of the precursor materials, or it may be separately charged into the mold and the precursor materials added afterwards. Careful control of the relative amounts of the various components and the reaction conditions may be desired to limit the amount of unreacted material in the composite. Post-cure processes known to those skilled in the art may also be employed. A partially polymerized precursor may be more completely polymerized or cross-linked after combination with the hydroxylated or aminated material or the included material. Alternatively or in addition, porosity may be introduced to the composite using foaming processes, e.g., by adding a porogen before or during polymerization, or by limiting the amount of water in the reaction vessel and applying vacuum during polymerization.

Alternatively or in addition, the various components may be combined and pressed in a Carver press or other compression molding device. Exemplary pressures include pressures ranging from about 1 psi to about 30,000 psi, including around 1,000 psi, around 10,000 psi, around 15,000 psi, around 20,000 psi, or around 25,000 psi. For melt casting applications, heat may be applied in conjunction with the pressure. In some embodiments, any temperature between 20° C. and about 300° C. may be used. One skilled in the art will recognize that higher temperatures may be needed, and that the processing temperature may be optimized to allow the polymer to be processed without damaging other components of the composite. The particular pressure to be used will depend on the materials being pressed.

In one embodiment, the components are tabletted together before being charged into a mold. For example, the components may be combined and fed into a tabletting apparatus. Any pharmaceutical tablet press may be used, for example, the Minipress available from Globe Pharma, Inc., of New Brunswick, N.J. The tablets enable a more uniform distribution of particulate included materials or particulate aminated/hydroxylated materials in the polymer matrix. The tabletting process produces tabs of a relatively uniform mass and composition. One or more tablets may be charged into a mold to be pressed into a composite.

Post-polymerization Processing

The surface of the composite may be modified after the polyurethane is polymerized. Some processing methods cause the surface of the composite to be primarily composed of polymer matrix rather than any included material. Abrasion methods are useful for exposing particulate included materials and provide surface roughness. Machining or cutting the composite will also expose particulates. Surface roughening may be accomplished mechanically, for example, through sanding, tumbling with a hard material such as sand, or the use of a pulsatile wave (e.g., the composite is conveyed above a liquid bath, and waves pulse the liquid into crests that contact the material). The desired surface texture may also be achieved using other machining methods, including but not limited to grinding, milling, cutting, broaching, drilling, laser etching, water cutting, and sand blasting. Chemical treatments may be used as well. Implants containing hydrolytically degradable polymers may be treated with water to pre-degrade the surface before implantation. The surface of the composite may also be modified to postpone cellular ingrowth. For example, the composite may be coated with a rapidly degradable or soluble material, or regions may be masked so that the polyurethane polymer is not exposed in certain regions during abrasive grinding, tumbling, sanding, etc. operations. The rate at which the surface of the composite is exposed may be adjusted such that the included material is revealed at a particular point in the healing cascade.

Of course, the composite may also be machined. In one embodiment, the composite is machined into a block which can be completely infiltrated by tissue within a predetermined time period. Alternatively, the composite may be machined into any desired shape and size. Exemplary shapes include sheet, plate, particle, sphere, hemisphere, strand, coiled strand, capillary network, film, fiber, mesh, disk, cone, portion of a cone, pin, screw, tube, cup, tooth, tooth root, bone, portion of bone, strut, wedge, portion of wedge, cylinder, threaded cylinder, rod, hinge, rivet, anchor, spheroid, ellipsoid, oblate spheroid, prolate ellipsoid, hyperbolic paraboloid. Composites may also be formed into the shape of a bone or a portion of a bone. Exemplary bones whose shape the composite may match in whole or in part (and which may be repaired or replaced using the techniques of the invention) include ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, incus, malleus, stapes, ilium, ischium, pubis, femur, tibia, fibula, patella, calcaneus, tarsal and metatarsal bones. In another embodiment, the composite is formed as a plate or similar support, including but not limited to an I-shape to be placed between teeth for intra-bony defects, a crescent apron for single site use, a rectangular bib for defects including both the buccal and lingual alveolar ridges, neutralization plates, spoon plates, condylar plates, clover leaf plates, compression plates, bridge plates, wave plates, etc. Partial tubular as well as flat plates may be fabricated using the techniques provided by the invention. Composites may be molded into any of these shapes as well, obviating a machining step or reducing the amount of machining needed.

In an alternative embodiment, bores or holes may be introduced into the composite. Such holes may be drilled after the composite is formed. Alternatively or in addition, the holes may be molded into place to introduce holes into the composite. Such holes may be used to provide an anchor for sutures, screws, or other fasteners, or as access channels for cellular penetration and bone remodeling. Of course, cells will also migrate into the hole after implantation.

The polyurethane composites of the invention may have a sufficient wet compressive strength to provide mechanical stability for an osteoimplant during healing. As the material degrades, it may retain some mechanical strength, for example, having at least 25 MPa, residual strength after 6 months in vivo. Alternatively, they may maintain at least 70% of their original strength after 8 or 24 weeks. In one embodiment, the composite exhibits stiffness in excess of 500 MPa, compressive strength in excess of 25 MPa, torsional strength in excess of 20 MPa, and bending strength exceeding 50 MPa. In another embodiment, the composite exhibits compressive strength exceeding 100 MPa, torsional strength exceeding 75 MPa, stiffness exceeding 5 GPa, and bending strength exceeding 150 MPa. For example, a bone void filler can transform quickly and need not have high mechanical strength, while a lumbar interbody implant may need to exhibit substantially higher compressive and fatigue strength as it is transformed. In some embodiments, a property of the polyurethane, e.g., mass, stiffness, torsional strength, bending strength, etc., may degrade at a rate of about 5%, about 10% or about 25% of original implant weight per month after implantation in vivo. In many embodiments, this degradation will be accompanied by an increase in the amount of or development of the mechanical properties of bony tissue at the implant site, thereby maintaining the overall mechanical strength of the material at the site. In some embodiments, especially where the expected loads on the implant are expected to be less (e.g, cranial implants), the transformation rate of the implant may be increased by adding porosity to the implant using the methods discussed above.

The mechanical properties desired for the composite and implants fabricated from the composite may depend on the application in which the implant will be used. One skilled in the art will understand how the compressive strength of the composite should be varied for other applications. Creep rates of less than 1% per 24 hours at 25 MPa (wet) after 24 hours or 10% per 24 hours after 3 months are desirable. In addition, humans apply about 1 to 1.1. million cycles of loading per year, from the activities of daily living (Morlock M, et al., Duration and frequency of every day activities in total hip patients. *J. Biomech*, (2001) 34:873-81). By assessing the healing time and adding a factor of safety, a desired fatigue period can be assessed. An exemplary target for interbody spinal applications is 10 million cycles at 1.5 kN or 5 million cycles at 3 kN. The applied stresses depend upon implant geometry but may range from, e.g., about 5 to about 30 MPa. Fatigue loading targets for other orthopedic applications may be as great or less. Maximum resolved shear and tensile strengths of 3 MPa or greater and absolute maximum resolved compressive strengths of 3 MPa or greater are also desirable. However, even if these mechanical properties are not present in the polymer or composite, the polymers and composites of the invention can be combined with other materials to modify their mechanical properties. In some embodiments, the mechanical strength, elastic modulus, and anisotropic properties of the implant can be tailored by adjusting the polymer chain length distribution, side chain length, degree of cross-linking, and/or physical processing.

EXAMPLES

Example #1

To determine the compressive strength of a composite implant made of approximately 66.6% bone and 33.3% castor bean polyurethane resin; 20 grams of bovine bone powder (particle size 120 µm-500 µm) were combined with a two part polyurethane (Doctors Research Group, Plymouth Conn. and described in "Vegetal Polyurethane Resin Implant Cranioplasty. Experimental Studies in Rabbits" by Luiz Fernando Francisco, Sao Jose do Rio Preto, 1998, which is incorporated herein by reference). Firstly, 6.10 grams of liquid comprising a polyisocyanate terminated molecule "prepolymer" were combined with 3.60 grams of a liquid comprising castor bean oil fatty acid triglyceride "diol". Next, bone particles were gradually mixed into the polyurethane solution, until the bone appeared well coated. The mixture was then packed by hand into three 5 cc syringes (packed with light hand pressure). The samples were then set aside to polymerize over a 48-hour period at room temperature. After polymerization was complete, the samples were removed from the syringes and cut to length (approx. 16 mm). Of the 4 samples tested; 2 were tested dry, while two were hydrated in Simulated Body Fluid (SBF) for 24 hours and tested wet. SBF solution contained 7.992-7.998 g NaCl, 0.2230-0.2243 g KCl, 0.2275-0.2289 g $K_2HPO_4.3H_2O$, 0.3041-0.3059 g $MgCl_2.6H_2O$, 36-40 ml HCl (1N), 0.3665-0.3687 g $CaCl_2.2H_2O$, 0.0708-0.0712 g $Na_2SO_4$, 0.3517-0.3539 g $NaHCO_3$, and deionized water to make 1000 ml, adjusted to a pH of 7.2-7.4 by a buffer solution of tris(hydroxymethyl)aminomethane. The results of mechanical static compression tests using the Bionix MTS 858 (Edin Prarrie Minn.) are shown in column 5 of Table 1. Results indicated a slight decrease in compressive strength (of about 7%) with the hydrated implants compared to the compressive strength of the dry implants, but load bearing capacity was still considered acceptable for use as an implant.

TABLE 1

| Sample | Length (mm) | Diameter (mm) | Weight (g) | Compressive Strength (MPa) |
|---|---|---|---|---|
| A-Dry | 16.74 | 11.85 | 2.70 | 72 |
| B-Dry | 16.58 | 11.84 | 2.64 | 72 |
| C-Wet | 16.68 | 11.87 | 2.63 | 66 |
| D-Wet | 16.70 | 11.87 | 2.63 | 67 |

Example #2

To determine the compressive strength of an implant made of 100% two-part castor bean polyurethane resin, (Doctors Research Group, Plymouth Conn. and described in "Vegetal Polyurethane Resin Implant Cranioplasty. Experimental Studies in Rabbits" by Luiz Fernando Francisco, Sao Jose do Rio Preto, 1998) enough of the prepolymer and diol (as indicated in Example 1) were mixed together to fill a 5 cc syringe. The material was hand packed into the syringe and allowed to polymerize for 18 hours at room temperature (air bubbles were noticed within the sample). After polymerization was complete, the samples were removed from the syringe and cut to length (approx. 13 mm). The results of mechanical static compression tests, using the Bionix MTS 858 (Edin Prarrie Minn.), are shown in column 5 of Table 2. The MPa values listed are only approximate at the point of visible plastic deformation of the implant. Samples did not mechanically fail at 20 MPa, but rather plastically deformed such that the test had to be stopped at approximately 50% strain. The load bearing capacity of the implants was still considered acceptable for use as an implant.

TABLE 2

| Sample ID | Length (mm) | Diameter (mm) | Weight (g) | Approximate Compressive Strength (MPa) |
|---|---|---|---|---|
| A-Dry | 12.96 | 8.55 | .78 | 20 |
| B-Dry | 13.97 | 8.52 | .81 | 20 |

Example #3

To determine the compressive strength of a composite implant made of approximately 75% bone and 25% castor bean polyurethane resin, 20 grams of bovine bone powder (particle size 120 µm-500 µm) were combined with a 6.82 grams of a two part polyurethane (Doctors Research Group, Plymouth Conn. and described in "Vegetal Polyurethane Resin Implant Cranioplasty. Experimental Studies in Rabbits" by Luiz Fernando Francisco, Sao Jose do Rio Preto, 1998). The mixture was then packed by hand into three 5 cc syringes (packed with light hand pressure). The samples were then set aside to polymerize over a 48-hour period at room temperature. After polymerization was complete, the samples were removed from the syringes and cut to length (approx. 14 mm). Of the 6 samples tested; 4 were tested dry, while two were hydrated in Simulated Body Fluid (SBF) for 24 hours and tested wet. The results of mechanical static compression tests using the Bionix MTS 858 (Edin Prarrie Minn.) are shown in column 5 of Table 3. Results indicated a decrease in compressive strength (of about 21.8%) with the hydrated implants compared to the compressive strength of the dry implants but load bearing capacity was still considered acceptable for use as an implant.

TABLE 3

| Sample ID | Length (mm) | Diameter (mm) | Weight (g) | Compressive Strength (MPa) |
|---|---|---|---|---|
| A1-Dry | 13.92 | 11.88 | 2.03 | 51 |
| A2-Dry | 14.02 | 11.87 | 2.14 | 56 |
| A3-Wet | 12.37 | 11.96 | 1.96 | 43 |
| B1-Dry | 14.16 | 11.86 | 2.25 | 59 |
| B2-Dry | 14.16 | 11.81 | 2.11 | 54 |
| B3-Wet | 14.34 | 11.92 | 2.23 | 43 |

Example #4

To determine if a composite implant could be made of bone with a lysine diisocyanate and castor bean polyurethane resin; 6 grams of a lysine diisocyanate were combined with 3.50 grams of a liquid comprising castor bean oil fatty acid triglyceride "the diol". Next, the mixture was heated to 93-95 degrees Celsius (on hot plate) and bone particles (particle size 120 µm-500 µm) were gradually mixed into the polyurethane solution, until the bone appeared well coated. The mixture was then packed by hand into 5 cc syringes (packed with light hand pressure). The samples were then set aside to polymerize over a 48-hour period at room temperature. The material polymerized into a material that could be extruded out of the syringe.

Example #5

3 grams of lysine diisocyanate were mixed with ProGenix Carrier #2 and at least partially polymerized to produce a flexible gel like sheet within a few hours.

Example #6

Tissue-derived materials are employed as chain extenders in polyurethanes. Exemplary formulations are given in Table 4. Ratios of polyol to isocyanate and of macropolyisocyanate to chain extender may be varied according to specific requirements of the desired biomaterial over a wide range, e.g., from about 10:1 to 1:10. A conventional polymerization catalyst known to those skilled in the art (such as an amine or tin compound) may or may not also be added, and the mixture is then combined with the crosslinking agent indicated and placed in a mold (such as Teflon) to polymerize. The percentage of the final composite comprised of composite filler (i.e., bone) may be varied between 5% and 95% according to the specific requirements of the biomaterial. The mixture polymerizes to form a bone-polyurethane composite. In one embodiment, calcium phosphate granules are substituted for the bone portion of the formulation. Exemplary preparations of calcium phosphates are described by U.S. Pat. No. 5,650,176 to Lee et al., U.S. Pat. No. 6,002,065 to Constantz et al., and U.S. Pat. No. 6,206,957 to Driessens et al., all of which are incorporated by reference herein. Additional calcium phosphates that may be exploited for use with the invention include but are not limited to α-tricalcium phosphate, hydroxyapatite, dicalcium phosphate, β-tricalcium phosphate, tetracalcium phosphate, amorphous calcium phosphate, and octacalcium phosphate. Substituted CaP phases are also contemplated for use with the invention, including but not limited to fluorapatite, chlorapatite, Mg-substituted tricalcium phosphate, and carbonate hydroxyapatite.

TABLE 4

| Polyol/polyamine (proportions by weight %) | Polyisocyanate | Chain extender (50% to 80% by weight) |
|---|---|---|
| Lecithin Starch Starch:Lecithin 15:85 Starch:Lecithin 85:15 Collagen | Hexamethylene Diisocyanate Uretdione polyisocyanate | Surface demineralized bone particles (200-1000 microns) |
| Polyactide Poly (ε-caprolactone) Hydroxy terminated polyethelene oxide Amine-terminated poly(1,4-butadiene) Tyrosine-based polycarbonate | Lysine diisocyanate ethyl ester Lysine diisocyanate | Calcium phosphate |
| Polylysine Polyserine Polytyrosine Glycerol Ethylene diamine | Cyclohexyl-diisocyanate Isocyanate terminated polysaccharide | Cartilage |

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:
1. A composite comprising:
a polyurethane polymer matrix; and particles embedded within the polyurethane polymer matrix,
wherein the polyurethane has a structure that results from a reaction of a polyisocyanate with one or more of a polyol or a polyamine; and the particles comprise a tissue material, an inorganic material, a bone substitute material, or any combination thereof.

2. The composite of claim 1, wherein the polyol or polyamine comprises a biomolecule.

3. The composite of claim 2, wherein the biomolecule is selected from the group consisting of phospholipids, fatty acids, cholesterols, polysaccharides, lecithin, starches, collagen, and any combination thereof.

4. The composite of claim 1, wherein the polyol or polyamine comprises an extracellular matrix material.

5. The composite of claim 1, wherein the polyol or the polyamine comprises a bioactive agent.

6. The composite of claim 1, wherein the polyol or the polyamine comprises a tissue material.

7. The composite of claim 6, wherein the tissue material comprises a bone particle.

8. The composite of claim 1, wherein the polyol or the polyamine comprises an inorganic material.

9. The composite of claim 1, wherein the polyol or the polyamine comprises a bone substitute material.

10. The composite of claim 1, wherein at least some of the particles are covalently linked with the polyurethane polymer matrix such that they are a chain extender.

11. The composite of claim 1, wherein the particles comprises a bone particle.

12. The composite of claim 11, wherein the bone particle comprises an elongated bone fiber.

13. The composite of claim 11, wherein the bone particle comprises a demineralized bone particle.

14. The composite of claim 13, wherein the demineralized bone particle are selected from the group consisting of a superficially demineralized bone particle, a partially demineralized bone particle, a fully demineralized bone particle, and any combination thereof 15. The composite of claim 1, comprising at least 10 weight percent of the particles.

16. The composite of claim 1, wherein the composite has a wet compressive strength of at least 3 MPa.

17. A method of making a composite, comprising a step of:
reacting a polyisocyanate with one or more of a polyol or a polyamine in the presence of particles to form a polyurethane polymer matrix having the particles embedded therein,
wherein the particles comprise a tissue material, an inorganic material, a bone substitute material, or any combination thereof.

18. The method of claim 17, wherein the particles are modified to increase surface concentration of hydroxyl or amine groups.

19. The method of claim 17, wherein the step of reacting comprises steps of:
mixing the polyisocyanate and the polyol or the polyamine to form a prepolymer;
adding the particles to form the polyurethane composite.

20. The method of claim 17, wherein reacting comprises steps of:
mixing the polyol or the polyamine with the particles;
adding the polyisocyanate to form the polyurethane composite.

21. The method of claim 17, wherein reacting comprises a step of:
mixing the polyisocyanate, the polyol or the polyamine and the particles to form the polyurethane composite.

* * * * *

(12) EX PARTE REEXAMINATION CERTIFICATE (9692nd)
United States Patent
Knaack et al.

(10) Number: US 7,985,414 C1
(45) Certificate Issued: Jun. 3, 2013

(54) POLYURETHANES FOR OSTEOIMPLANTS

(75) Inventors: David Knaack, Summit, NJ (US); John Winterbottom, Jackson, NJ (US); David Kaes, Toms River, NJ (US); Todd Boyce, Matawan, NJ (US); Larry Shimp, Morganville, NJ (US)

(73) Assignee: Warsaw Orthopedic, Inc., Warsaw, IN (US)

Reexamination Request:
No. 90/012,251, Apr. 12, 2012

Reexamination Certificate for:
Patent No.: 7,985,414
Issued: Jul. 26, 2011
Appl. No.: 11/336,127
Filed: Jan. 19, 2006

Related U.S. Application Data

(63) Continuation-in-part of application No. 10/771,736, filed on Feb. 4, 2004, now Pat. No. 8,002,843.

(60) Provisional application No. 60/444,759, filed on Feb. 4, 2003.

(51) Int. Cl.
*A61K 31/785* (2006.01)
*A61K 31/795* (2006.01)
*A61L 27/34* (2006.01)
*A61L 27/54* (2006.01)

(52) U.S. Cl.
USPC .................................. 424/422; 424/78.27

(58) Field of Classification Search
None
See application file for complete search history.

(56) References Cited

To view the complete listing of prior art documents cited during the proceeding for Reexamination Control Number 90/012,251, please refer to the USPTO's public Patent Application Information Retrieval (PAIR) system under the Display References tab.

*Primary Examiner* — Gary Kunz

(57) ABSTRACT

Biological-based polyurethanes and methods of making the same. The polyurethanes are formed by reacting a biodegradable polyisocyanate (such as lysine diisocyanate) with an optionally hydroxylated biomolecule to form polyurethane. The polymers formed may be combined with ceramic and/or bone particles to form a composite, which may be used as an osteoimplant.

US 7,985,414 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2 and 4-21 are determined to be patentable as amended.

Claim 3, dependent on an amended claim, is determined to be patentable.

New claims 22-27 are added and determined to be patentable.

1. A composite comprising:
   a *biodegradable* polyurethane polymer matrix; and
   particles embedded within the polyurethane polymer matrix,
   wherein the polyurethane has a structure that results from a reaction of a *biocompatible* polyisocyanate with [one or more of] a polyol [or a polyamine] *in the presence of the particles*; and the particles comprise a [tissue] *bone* material, [an inorganic material,] a bone substitute material, or any combination thereof.

2. The composite of claim 1, wherein the polyol [or polyamine] comprises a biomolecule.

4. The composite of claim 1, wherein the polyol [or the polyamine] comprises [an extracellular matrix material] *collagen*.

5. The composite of claim 1, wherein the polyol [or the polyamine] comprises a bioactive agent.

6. The composite of claim 1, wherein the polyol [or the polyamine] comprises [a tissue] *bone* material.

7. The composite of claim [6] *1*, wherein the [tissue material comprises a bone particle] *particles comprise ceramic*.

8. The composite of claim 1, wherein the polyol [or the polyamine] comprises [an inorganic material] *hydroxyapatite*.

9. The composite of claim 1, wherein the polyol [or the polyamine] comprises a bone substitute material.

10. The composite of claim 1, wherein [at least some of] the particles [are covalently linked with the polyurethane polymer matrix such that they are a chain extender] *comprise bone powder*.

11. The composite of claim 1, wherein the particles [comprises] *comprise* a bone [particle] *fiber*.

12. The composite of claim 11, wherein the [bone particle comprises] *particles comprise* an elongated bone fiber.

13. The composite of claim [11] *1*, wherein the [bone particle comprises] *particles comprise* a demineralized bone particle.

14. The composite of claim 13, wherein the demineralized bone [particle] *particles* are selected from the group consisting of a superficially demineralized bone particle, a partially demineralized bone particle, a fully demineralized bone particle, and any combination thereof.

15. The composite of claim 1, comprising at least [10] *30* weight percent of the particles.

16. The composite of claim 1, wherein the composite has a wet compressive strength of at least [3] *50* MPa.

17. A method of making a composite, comprising a step of:
    reacting a *biocompatible* polyisocyanate with [one or more of] a polyol [or a polyamine] in the presence of particles to form a *biodegradable* polyurethane polymer matrix having the particles embedded therein,
    wherein the particles comprise [a tissue material] *bone* material, [an inorganic material,] a bone substitute material, or any combination thereof.

18. The method of claim 17, wherein the particles [are modified to increase surface concentration of hydroxyl or amine groups] *comprise demineralized bone*.

19. The method of claim 17, wherein the step of reacting comprises steps of:
    mixing the polyisocyanate and the polyol [or the polyamine] to form a [prepolymer] *mixture*;
    adding the particles to *the mixture to* form the polyurethane composite.

20. The method of claim 17, wherein reacting comprises steps of:
    mixing the polyol [or the polyamine] with the particles;
    adding the polyisocyanate to form the polyurethane composite.

21. The method of claim 17, wherein reacting comprises a step of:
    mixing the polyisocyanate, the polyol [or the polyamine] and the particles to form the polyurethane composite.

*22. The composite of claim 1, wherein the composite comprises polycaprolactone.*

*23. The method of claim 17, wherein the composite comprises polycaprolactone.*

*24. The composite of claim 1, wherein the biocompatible polyisocyanate comprises lysine diisocyanate.*

*25. The method of claim 17, wherein the biocompatible polyisocyanate comprises lysine diisocyanate.*

*26. The composite of claim 1, wherein the composite comprises glucose.*

*27. The method of claim 17, wherein the composite comprises glucose.*

\* \* \* \* \*

(12) EX PARTE REEXAMINATION CERTIFICATE (10157th)
United States Patent
Knaack et al.

(10) Number: US 7,985,414 C2
(45) Certificate Issued: May 9, 2014

(54) POLYURETHANES FOR OSTEOIMPLANTS

(75) Inventors: David Knaack, Summit, NJ (US); John Winterbottom, Jackson, NJ (US); David Kaes, Toms River, NJ (US); Todd Boyce, Matawan, NJ (US); Larry Shimp, Morganville, NJ (US)

(73) Assignee: Warsaw Orthopedic, Inc., Warsaw, IN (US)

Reexamination Request:
No. 90/012,932, Jul. 26, 2013

Reexamination Certificate for:
Patent No.: 7,985,414
Issued: Jul. 26, 2011
Appl. No.: 11/336,127
Filed: Jan. 19, 2006

Reexamination Certificate C1 7,985,414 issued Jun. 3, 2013

Related U.S. Application Data

(63) Continuation-in-part of application No. 10/771,736, filed on Feb. 4, 2004, now Pat. No. 8,002,843.

(60) Provisional application No. 60/444,759, filed on Feb. 4, 2003.

(51) Int. Cl.
| | |
|---|---|
| *A61F 13/00* | (2006.01) |
| *A61K 31/74* | (2006.01) |
| *C08G 18/79* | (2006.01) |
| *C08G 18/77* | (2006.01) |
| *A61K 31/785* | (2006.01) |
| *A61L 27/46* | (2006.01) |
| *A61L 27/48* | (2006.01) |
| *C08G 18/10* | (2006.01) |
| *C08G 18/38* | (2006.01) |
| *C08G 18/64* | (2006.01) |
| *C08G 18/73* | (2006.01) |
| *A61L 27/18* | (2006.01) |
| *C08L 75/04* | (2006.01) |
| *C08G 18/36* | (2006.01) |
| *A61F 2/28* | (2006.01) |

(52) U.S. Cl.
CPC ............ *C08G 18/798* (2013.01); *C08G 18/771* (2013.01); *A61K 31/785* (2013.01); *A61F 2002/2817* (2013.01); *A61L 27/46* (2013.01); *A61L 27/48* (2013.01); *C08G 18/10* (2013.01); *C08G 18/3882* (2013.01); *C08G 18/6484* (2013.01); *C08G 18/73* (2013.01); *A61L 27/18* (2013.01); *C08L 75/04* (2013.01); *C08G 2230/00* (2013.01); *C08G 18/36* (2013.01); *A61F 2/28* (2013.01)
USPC .......................................... 424/422; 424/78.27

(58) Field of Classification Search
None
See application file for complete search history.

(56) References Cited

To view the complete listing of prior art documents cited during the proceeding for Reexamination Control Number 90/012,932, please refer to the USPTO's public Patent Application Information Retrieval (PAIR) system under the Display References tab.

*Primary Examiner* — Dwayne Jones

(57) ABSTRACT

Biological-based polyurethanes and methods of making the same. The polyurethanes are formed by reacting a biodegradable polyisocyanate (such as lysine diisocyanate) with an optionally hydroxylated biomolecule to form polyurethane. The polymers formed may be combined with ceramic and/or bone particles to form a composite, which may be used as an osteoimplant.

US 7,985,414 C2

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-3, 7-9, 15, 17 and 19-27 is confirmed.

New claims 28-43 are added and determined to be patentable.

Claims 4-6, 10-14, 16 and 18 were not reexamined.

28. *The composite of claim 1, wherein the particles increase compressive strength of the composite.*

29. *The method of claim 17, wherein the particles increase compressive strength of the composite.*

30. *The composite of claim 1, wherein the particles reinforce the composite.*

31. *The method of claim 17, wherein the particles reinforce the composite.*

32. *The composite of claim 1, wherein the particles have a particle size range of from about 0.05 to about 1.2 mm.*

33. *The method of claim 17, wherein the particles have a particle size range of from about 0.05 to about 1.2 mm.*

34. *The composite of claim 1, wherein the polyisocyanate is resorbable.*

35. *The method of claim 17, wherein the polyisocyanate is resorbable.*

36. *The composite of claim 1, wherein the polyol comprises polyethylene glycol.*

37. *The method of claim 17, wherein the polyol comprises polyethylene glycol.*

38. *The composite of claim 1, wherein the composite allows ingrowth of bone as the composite degrades.*

39. *The method of claim 17, wherein the composite allows ingrowth of bone as the composite degrades.*

40. *The composite of claim 1, wherein the composite allows bone remodeling.*

41. *The method of claim 17, wherein the composite allows bone remodeling.*

42. *The composite of claim 1, wherein the composite has a compressive strength of at least 3 MPa.*

43. *The method of claim 17, wherein the composite has a compressive strength of at least 3 MPa.*

\* \* \* \* \*